(12) United States Patent
Brown

(10) Patent No.: US 11,246,750 B2
(45) Date of Patent: Feb. 15, 2022

(54) ICE THERAPY METHOD AND APPARATUS

(71) Applicant: James E. Brown, Alexandria, VA (US)

(72) Inventor: James E. Brown, Alexandria, VA (US)

( * ) Notice: Subject to any disclaimer, the term of this patent is extended or adjusted under 35 U.S.C. 154(b) by 262 days.

(21) Appl. No.: 16/018,850

(22) Filed: Jun. 26, 2018

(65) Prior Publication Data

US 2019/0388268 A1    Dec. 26, 2019

(51) Int. Cl.
  *A61F 7/00* (2006.01)
  *A61F 7/02* (2006.01)
  *A61F 7/10* (2006.01)

(52) U.S. Cl.
  CPC .......... *A61F 7/0241* (2013.01); *A61F 7/0085* (2013.01); *A61F 7/10* (2013.01); *A61F 2007/0056* (2013.01); *A61F 2007/0215* (2013.01)

(58) Field of Classification Search
  CPC ........ A61F 7/0241; A61F 7/0085; A61F 7/10; A61F 2007/0215; A61F 2007/0056; A61F 7/103; A61F 2007/0268
  See application file for complete search history.

(56) References Cited

U.S. PATENT DOCUMENTS

| | | | |
|---|---|---|---|
| 1,896,953 A | 2/1933 | Hassell | |
| 1,902,016 A | 3/1933 | Copeman | |
| 3,916,911 A | 11/1975 | Sauder et al. | |
| 4,149,529 A * | 4/1979 | Copeland | A61H 9/0078 601/151 |
| 4,170,998 A | 10/1979 | Sauder | |
| 5,337,579 A * | 8/1994 | Saia, III | B60H 1/3226 62/239 |
| 5,476,489 A | 12/1995 | Koewler | |
| 5,806,335 A * | 9/1998 | Herbert | A61F 7/10 607/114 |
| 6,086,609 A * | 7/2000 | Buckley | A61F 7/10 607/104 |
| 7,008,445 B2 | 3/2006 | Lennox | |
| 8,613,762 B2 | 12/2013 | Bledsoe | |
| 8,979,777 B2 | 3/2015 | Gammons | |
| 9,402,763 B2 | 8/2016 | Bledsoe | |

(Continued)

OTHER PUBLICATIONS

Youtube video clip entitled "How to Build a Beer Fridge (Kegerator Conversion Kit)," uploaded on May 5, 2015 by user "KegWorks." Retrieved from Internet https://www.youtube.com/watch?v=W9UW-QLg9d0. (Year: 2015).*

*Primary Examiner* — Linda C Dvorak
*Assistant Examiner* — Yasamin Ekrami
(74) *Attorney, Agent, or Firm* — Bacon & Thomas, PLLC

(57) ABSTRACT

A method of using an ice therapy machine involves replacing water with windshield washer fluid containing ethanol or ethylene glycol, and placing the main unit of the ice therapy machine, including the ice chest and pump, in a freezer to prevent the ice in the ice chest from melting. The freezer has been modified to include openings for passage of the fluid-circulating tubes of the ice therapy machine, and an opening for the power cord of the ice therapy machine, which supplies power to the pump. Alternatively, the door of the freezer may be replaced by an insulated panel having openings for the coolant circulating tubes and power cord. An on/off switch may be installed in the power cord so that the pump can be turned on and off without having to open the freezer door.

4 Claims, 3 Drawing Sheets

(56) References Cited

U.S. PATENT DOCUMENTS

| | | |
|---|---|---|
| 2005/0107855 A1* | 5/2005 | Lennox ................... A61F 7/10 607/104 |
| 2006/0287697 A1* | 12/2006 | Lennox ................ A61F 7/0085 607/96 |
| 2008/0269852 A1* | 10/2008 | Lennox ................... A61F 7/02 607/104 |
| 2010/0145421 A1 | 6/2010 | Tomlinson et al. |
| 2012/0245661 A1 | 9/2012 | Mason |
| 2013/0245729 A1 | 9/2013 | Edelman et al. |
| 2014/0074198 A1* | 3/2014 | Bledsoe ................... A61F 7/10 607/104 |
| 2016/0317348 A1* | 11/2016 | Banker ................ A61H 9/0078 |
| 2017/0246031 A1 | 8/2017 | Benyaminpour et al. |
| 2017/0252534 A1* | 9/2017 | Nofzinger ............ A61H 9/0007 |

\* cited by examiner

ICE THERAPY METHOD AND APPARATUS

BACKGROUND OF THE INVENTION

1. Field of the Invention

The invention relates to a method and apparatus for enhancing the efficiency and convenience of an ice therapy machine.

2. Description of Related Art

Conventional ice therapy machines are used to provide the cooling effect of an ice pack, but with the convenience of maintaining the cold temperature by continuously circulating near-freezing water through a pad that wraps around the injured body part.

An example of a conventional, commercially available, ice therapy machine is the "Cold Rush Cold Therapy System" sold by Ossur Americas, Inc., which includes a main unit containing a pump, a therapy pad that is placed around or against a body part, and hoses that connect the pump to the pad and circulate water through the pad. The water is chilled by ice placed by the user into the main unit. The chilled circulating water and therapy pad provide a more convenient and uniform cold temperature therapy than is possible with direct placement of ice packs or frozen objects on the site of the injury, particularly when cold therapy is required for an extended period of time.

A disadvantage of the conventional ice therapy machine is that the ice in the ice chest will melt as the water circulates past and absorbs heat from the injury. This problem is exacerbated if the ice is in the form of crushed ice, which is the most convenient source of ice. As a result, the melted ice must be frequently replaced with fresh ice, and the replacement ice must be stored by the user until read for use.

In addition, unlike a traditional ice pack, the therapy pad of an ice therapy machine cannot achieve a temperature of less than 32 degrees since the water circulating through the pad would freeze or turn to slush at sub-freezing temperatures, and therefore the machine would no longer be able to circulate the water.

Still further, it may be difficult just to maintain a therapeutically useful above-freezing temperature even with frequent ice replacement if the injury is large and highly inflamed. The larger the area of the injury, and the greater the heat-generating inflammation, the greater the amount of heat transferred to the water circulating through the therapy pad. When the water warms too rapidly, the amount of time spent circulating through the ice chest may be insufficient to maintain the desired temperature.

One solution to the problem of achieving and maintaining colder temperatures in the pad would be to replace water with antifreeze (propylene glycol), which is capable of achieving a temperature of below 32° Fahrenheit without freezing, and of maintaining the sub-freezing temperature for a greater length of time than water. However, antifreeze is generally a highly toxic material and gives off noxious fumes that make it unsuitable for use in a consumer product such as an ice therapy machine. As a result, antifreeze has been reserved for specially designed machines used in an outdoor setting, such as the propylene glycol circulating therapy device for horses disclosed in U.S. Pat. No. 6,086,609, or the "refrigerant" circulating device, also for horses, disclosed in U.S. Pat. No. 3,916,911.

As to the problem of having to frequently replace the ice in the ice therapy machine, one could entirely replace the ice chest, tray, or compartment of the commercially available ice therapy machine with a compressor and evaporator, i.e., a traditional refrigeration cycle, as disclosed for example in U.S. Pat. No. 6,086,609 (cited above) and U.S. Pat. No. 4,170,998. However, such machines can cost tens of thousands of dollars or more and thus are mainly suitable for use in hospitals. The reason for using ice chests rather than a compression-evaporation refrigeration cycle in cold therapy machines intended for home or consumer use is that a cooling effect can be achieved at far less cost by using ice as the primary source of cold rather than a built-in electrical cooling apparatus.

To solve these problems with conventional cold therapy machines, it would be desirable to combine the cooling efficiency of a cooling therapy machine having its own cooling components and thermostatic control, such as used in hospitals, with the low cost and convenience of a commercially available, consumer-grade ice therapy machine such as the Ossur Cold Rush Cold Therapy System described above, preferably without the need to make substantial modifications to the conventional machine. However, to date, the optimal combination of convenience, effectiveness, and low cost has yet to be achieved.

Finally, by way of background, U.S. Pat. Nos. 8,979,777; 5,806,335; and 5,476,489 and U.S. Patent Publication No. 2012/0245661 are directed to ice therapy machines similar to the Ossur machine, including ice chests and circulating water as a coolant.

SUMMARY OF THE INVENTION

It is an objective of the invention to provide a way to reduce the frequency that the ice in a conventional, commercially available ice therapy machine must be changed, without modifying the machine itself.

It is a second objective the invention to provide a way to increase the efficiency of the conventional, commercially available ice therapy machine so that it can maintain a desired low temperature for an extended period of time and thereby improve therapeutic effect and convenience.

These objectives are achieved by an improved method of using an ice therapy machine, and an apparatus for implementing the improved method, that involves replacing the water with a safe ethylene glycol mixture, commonly used as a windshield washer fluid, and by placing the entire cold therapy machine, including the ice chest and pump, in a freezer and operating the machine while the machine is in the freezer to prevent the ice in the ice chest from melting and avoid the need to replace the melted ice during a cold therapy session. To prevent the ice from diluting the ethylene glycol, the ice is preferably contained within a plastic container, such as a 16-24 oz. ice pack, which also helps maintain the fluid at a consistently colder temperature. Since the ethylene glycol mixture remains liquid at temperatures under 32 degrees, the temperature of the freezer can also be set to a temperature lower than 32 degrees if desired.

In a preferred embodiment of the invention, the freezer is a relatively small portable freezer or refrigerator/freezer unit that has been modified to include openings for passage of the fluid-circulating tubes of the ice therapy machine, and an opening for the power cord of the ice therapy machine, which supplies power to the pump. Alternatively, the door of the freezer may be replaced by an insulated panel having openings for the coolant circulating tubes and power cord.

For greater convenience, an on/off switch may be installed in the power cord so that the pump can be turned on and off without having to open the freezer door. The on/off switch of the ice therapy machine can then be left on while it is in the freezer.

DETAILED DESCRIPTION OF THE PREFERRED EMBODIMENTS

Throughout the following description and drawings, like reference numbers/characters refer to like elements. It should be understood that, although specific exemplary embodiments are discussed herein there is no intent to limit the scope of present invention to such embodiments. To the contrary, it should be understood that the exemplary embodiments discussed herein are for illustrative purposes, and that modified and alternative embodiments may be implemented without departing from the scope of the present invention.

Figure 1:
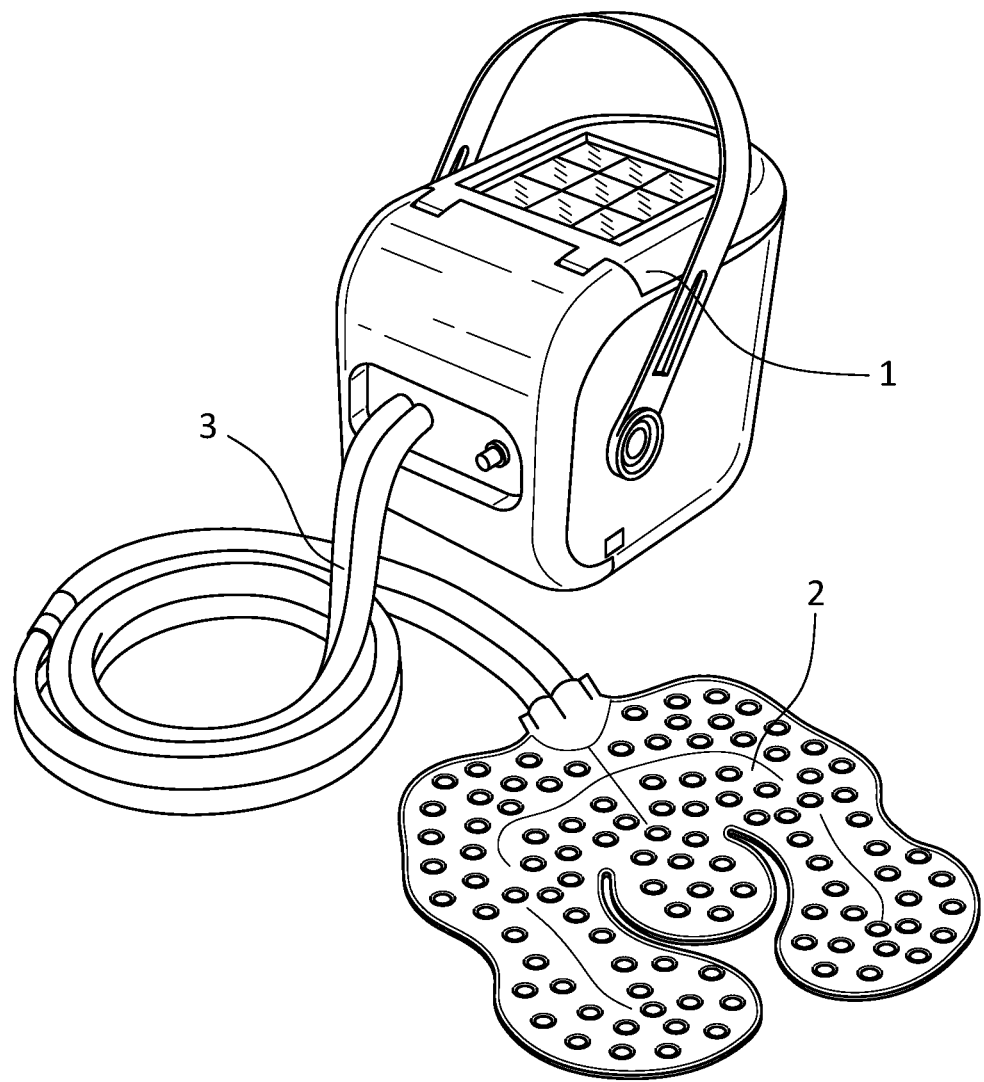
FIG. 1 shows a conventional ice therapy machine.

FIG. 1 shows a conventional ice therapy machine, which includes a main ice/pump unit 1 into which ice is placed to chill water circulated by a pump (not shown), a therapy pad 2 that is placed in contact with a body part and through which the chilled water is circulated to provide a therapeutic cooling effect, and hoses 3 that connect the pump and the therapy pad 2. The size and shape of the therapy pad may be varied depending on the body part to be treated.

Figure 2:
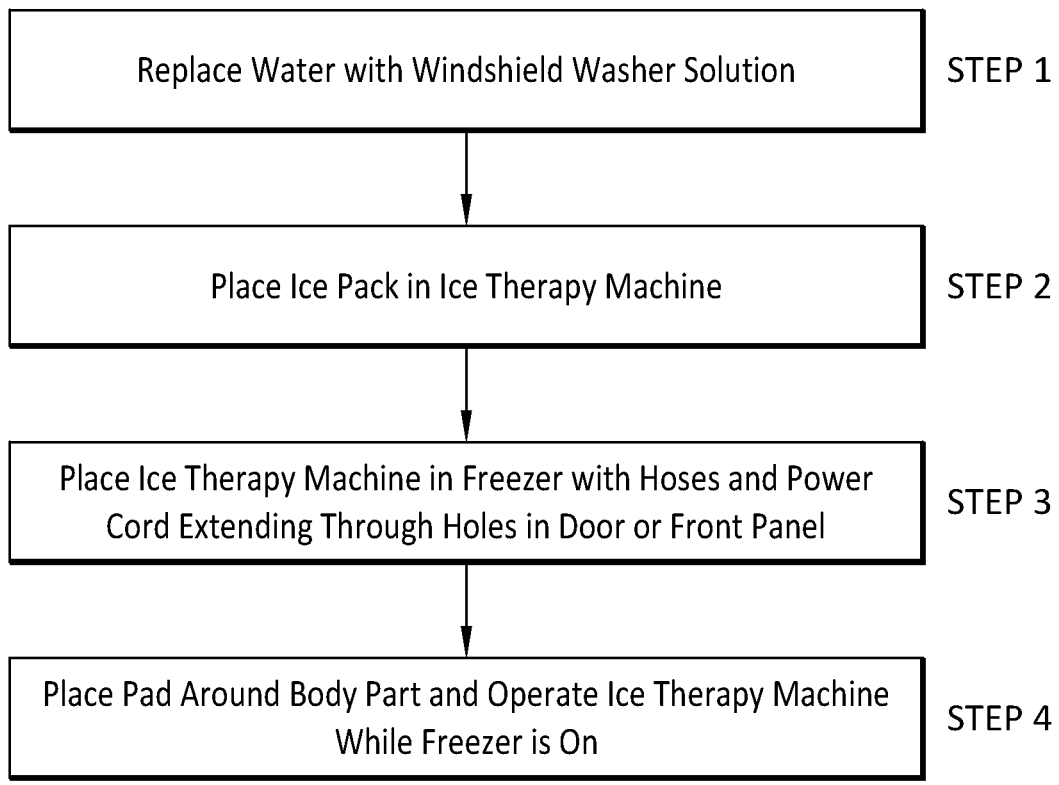
FIG. 2 is a flowchart illustrating a method of using an ice therapy machine in accordance with the principles of a preferred embodiment of the invention.

According to the preferred method illustrated in FIG. 2, the water that circulates through the hoses 3 and therapy pad 2 is replaced by a windshield washer solution of ethylene glycol (step 1) and the main ice/pump unit 1 of the conventional ice therapy machine is placed in a freezer (step 2). The freezer preferably includes an adjustable thermostat to enable control of the temperature. Ice, for example provided in a sealed 16-24 oz. ice pack, is placed in the main ice/pump unit 1 and the freezer is turned on (either before or after placement of ice in the unit) to keep the ice in the ice pack from melting (step 3). The therapy pad is positioned on a body part to be treated and the main ice/pump unit 1 is turned on and operated according to directions for operation of the unit (step 4). Operation may continue as long as necessary for therapeutic purposes without having to add ice to the main ice/pump unit.

Figure 3:
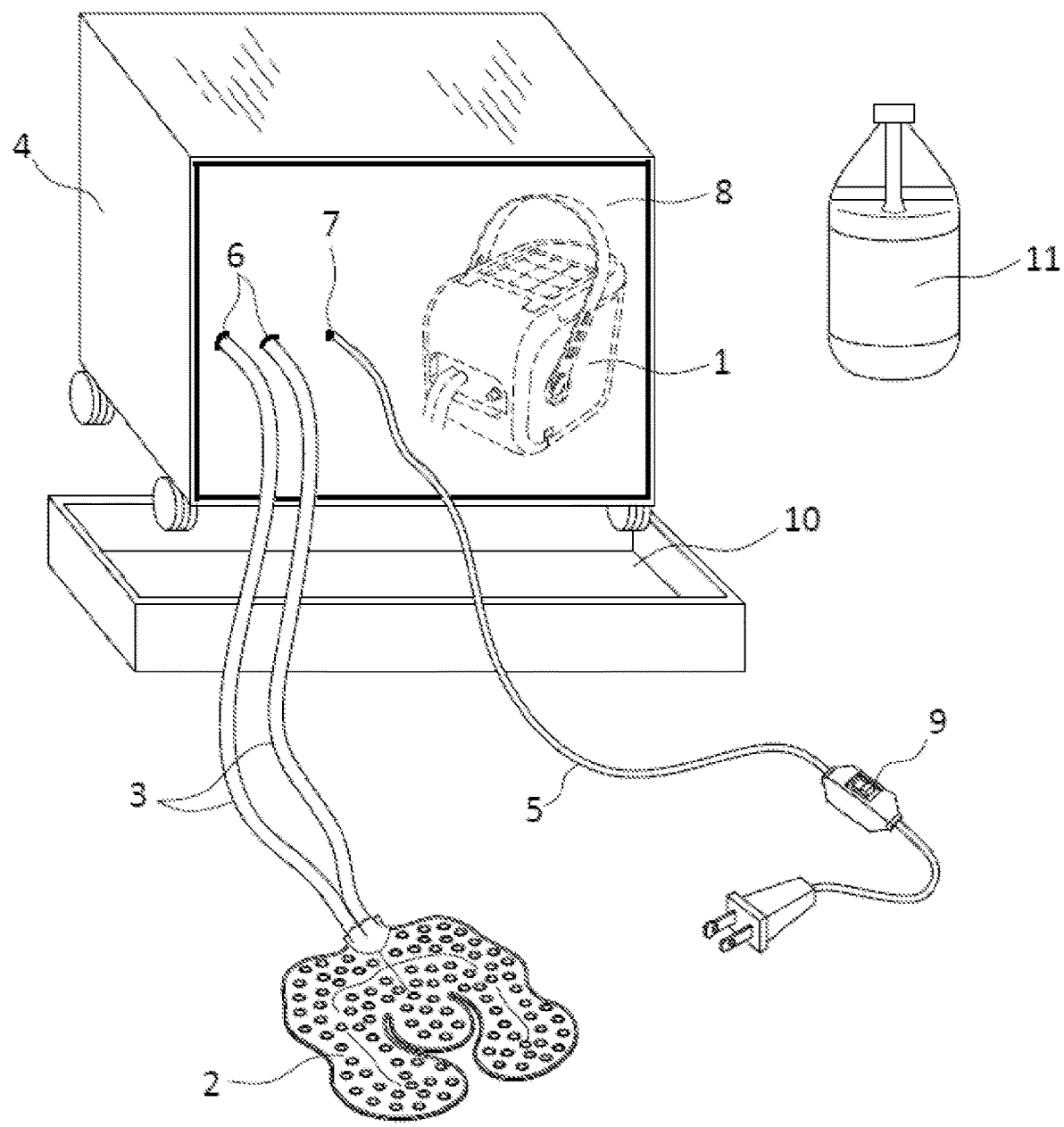
FIG. 3 is a diagram of an apparatus for implementing the method of the invention, showing a freezer that has been modified to accommodate an ice therapy machine by providing openings for hoses and a power cord.

FIG. 3 shows an apparatus for implementing the method of FIG. 2. The apparatus includes a freezer 4 and the conventional main ice/pump unit 1, which has been placed inside freezer 4. The main ice/pump unit 1, therapy pad 2, and hoses 3 may be parts of an unmodified, commercially available ice therapy machine.

In order to permit the hoses 3 and power cord 5 to extend from inside the freezer 4 to the therapy pad 2, respective holes 6 and 7 are cut in the door 8 of the freezer, or the original door 6 is replaced by an insulating panel made, for example, of Styrofoam or a similar material with preformed holes. If the ice therapy machine includes a wired remote control (not shown), additional holes (not shown) may be cut to permit the wired remote control to be used from outside the freezer. In addition, for convenience, an on/off switch 9 may be added to the power cord, or provided at the wall outlet into which the power cord is plugged, so that the ice therapy machine can be turned on and off without opening or removing the freezer door 8 or insulated door-replacing panel. Optionally, an emergency drainage tray 10 may be placed under the freezer 4.

Finally, FIG. 3 also shows a bottle or jug 11 of "blue" windshield washer fluid made up of a solution of ethylene glycol and water, and which replaces water as the fluid that circulates through the pad. For machines that use melted ice water as the circulating fluid, the windshield wiper fluid may be poured directly into the space containing the ice. Although an ethylene glycol solution is preferred, it is within the scope of the invention to include components other than ethylene glycol in the windshield washer fluid that replaces water as the heat transfer fluid.

It will be appreciated that the term "ice pack" as used herein, which is placed in the ice therapy machine to cool the ethylene glycol solution, is not required to contain water. The ice pack is a commercially available item that may contain fluids other than pure water.

What is claimed is:

1. A method of using a cold therapy machine, the cold therapy machine having an ice container for filling with ice and a pump configured to be connected to hoses for circulating a fluid having a temperature below 32 degrees Fahrenheit through a therapy pad arranged to be placed in contact with a body part, comprising the steps of:
   placing ice in the container, and placing the cold therapy machine, including the ice container, and the pump, into a freezer;
   extending hoses from the therapy pad, which is located outside the freezer, through holes in the door of the freezer;
   connecting the pump to the hoses and closing the freezer door, such that the hoses extend from the pump through the holes in the door of the freezer to the therapy pad;
   operating the freezer; and
   while operating the freezer, operating the pump to circulate the fluid through the hoses from the ice therapy machine to the therapy pad and back to the ice therapy machine,
   wherein the fluid is a fluid mixture that remains liquid at temperatures below 32 degrees Fahrenheit.

2. A method as claimed in claim 1, wherein the fluid mixture is an ethylene glycol solution.

3. Apparatus for enhancing efficiency of an ice therapy machine and eliminating a need to add ice to the ice therapy machine during a therapy session, comprising:
   a freezer in which the ice therapy machine is placed, the ice therapy machine including an ice container and a pump, and the pump being connected to hoses for circulating fluid from the ice therapy machine through a door or insulating front panel of the freezer to a therapy pad situated outside the freezer for placement on a body part to be treated, and for circulating the fluid from the therapy pad back through the door or insulating front panel to the ice therapy machine,
   wherein the door or insulating front panel has at least one hose-passing hole configured to enable passage of the hoses, and a power cord hole configured to enable passage of a power cord for the ice therapy machine to supply power to operate the ice therapy machine from outside the freezer while the ice therapy machine is situated within the freezer, and
   wherein the fluid is a fluid mixture that remains liquid at temperatures under 32 degrees Fahrenheit.

4. Apparatus as claimed in claim 3, further comprising an on/off switch connected to the power cord for turning the pump on and off from outside the freezer.

\* \* \* \* \*